[19] United States Patent
Watson

[11] Patent Number: 4,649,913
[45] Date of Patent: Mar. 17, 1987

[54] TRACHEOSTOMY TUBE ASSEMBLIES
[75] Inventor: Jeremy P. Watson, Folkestone, England
[73] Assignee: Smiths Industries Public Limited Company, London, England
[21] Appl. No.: 757,426
[22] Filed: Jul. 8, 1985
[30] Foreign Application Priority Data
  Jul. 31, 1984 [GB] United Kingdom ................ 8419510
[51] Int. Cl.⁴ .......................................... A61M 16/00
[52] U.S. Cl. ........................ 128/207.14; 128/207.15; 128/207.17; 604/338; 604/174
[58] Field of Search ...................... 128/207.14, 207.15, 128/207.17, 200.26, 206.26, 207.18, 202.28, 206.24; 604/174, 337, 338

[56] References Cited
U.S. PATENT DOCUMENTS

| 1,835,757 | 12/1931 | Burchett | 128/207.17 |
| 3,137,299 | 6/1964 | Tabor | 128/351 |
| 3,889,688 | 6/1975 | Eamkaow | 128/207.15 |
| 3,973,569 | 8/1976 | Sheridan | 128/351 |
| 4,449,523 | 5/1984 | Szachowicz et al. | 128/207.15 |
| 4,449,526 | 5/1984 | Elam | 128/207.14 |
| 4,459,984 | 7/1984 | Liegner | 128/207.15 |
| 4,559,940 | 12/1985 | McGinnis | 128/206.26 |

FOREIGN PATENT DOCUMENTS
2028139  3/1980  United Kingdom .

Primary Examiner—Henry J. Recla
Attorney, Agent, or Firm—Pollock, Vande Sande and Priddy

[57] ABSTRACT

A tracheostomy tube assembly has a tube the forward end of which is located within the trachea and supports an inflatable sealing cuff. The rear end of the assembly supports a soft, semi-flexible flange having slots which receive a tape by which the assembly is secured about the patient's neck. The assembly also carries a second inflatable plastics cuff mounted on the flange, which encircles the tube and has a raised portion on opposite sides of the tube. The volume of the second cuff, when inflated, is sufficient to accommodate the space between the flange and the neck without elastic deformation of the cuff.

8 Claims, 3 Drawing Figures

TRACHEOSTOMY TUBE ASSEMBLIES

BACKGROUND OF THE INVENTION

This invention relates to tracheostomy tube assemblies.

Tracheostomy tubes are used to provide ventilation, or to administer anaesthetic gas to a patient's trachea, via an opening, or stoma, in the patient's throat. The tube is bent at about 90 or 110 degrees and its forward end can be provided with an inflatable cuff that seals the outside of the tube with the patient's trachea. The rear end of the tube emerges through the opening in the patient's throat and has a flange which is used to secure the tube in position by means of a collar passed around the neck, or an adhesive tape. The rear end of the tube is either left open to allow the patient to breathe freely through the tube, or is connected to a ventilating machine to enable forced ventilation.

Because the build of patients varies one from the other, the flange by which the tube is secured is not usually located in the ideal position. For a patient with a thick layer of tissue between his trachea and the surface of his neck, the length of the standard tube is such that the cuff may not be located correctly in the trachea, thereby leading to a poor seal. For patients with a thinner layer of tissue, the flange may be spaced by a gap from the neck surface. With such a patient, if the flange is pushed against the neck, the forward end of the tube may contact the trachea wall, leading to abrasion and possible stenosis. To reduce this, the flange may be left spaced from the neck and gauze padding can be placed between the flange and the patient's neck. This can, however, provide a site for infection.

Various arrangements have been proposed to provide the tracheostomy tube with a flange that can be moved along the tube, making it adjustable to the best position for each patient. These arrangements, however, are not generally satisfactory for several reasons. Because the surface of the tube is smooth and can be wet, it is difficult to produce a flange that can be locked securely relative to the tube, and that can also be displaced freely for positioning purposes. Some adjustable flanges have a tendency to twist the tube when they are locked or unlocked and can be uncomfortable to the patient.

BRIEF SUMMARY OF THE INVENTION

It is one object of the present invention to provide a tracheostomy tube assembly that enables simple adjustment of the assembly for different patients and that can be used to avoid the above-mentioned disadvantages.

According to the present invention there is provided a tracheostomy tube assembly having a tube with a forward end that is adapted for insertion within a patient's trachea and a rear end that emerges through an opening in the patient's neck, the rear end being provided with a flange by which the tube assembly is secured to the patient's neck, the assembly including at least one inflatable cuff located externally of the tube and located intermediate the flange and the patient's neck such that, by inflating the cuff, any space between the flange and the patient's neck can be accommodated.

Preferably the cuff encircles the tube and may have a raised portion on opposite sides of the tube. The volume of the cuff when inflated is preferably sufficient to accommodate the space between the flange and the neck without elastic deformation of the cuff. The cuff may be secured to the flange and be of a plastics material.

The flange may be of a soft, semi-flexible material and be formed with slots adapted to receive a tape by which the assembly can be secured to the patient's neck.

A tracheostomy tube assembly in accordance with the present invention, will now be described, by way of example, with reference to the accompanying drawings.

DETAILED DESCRIPTION

Figure 1:
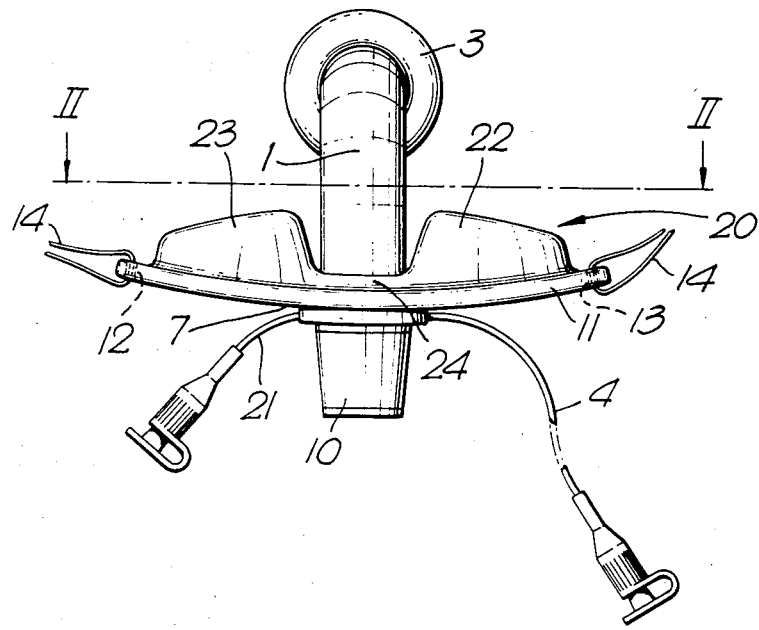
FIG. 1 is a plan view of the tracheostomy tube assembly.
Figure 2:
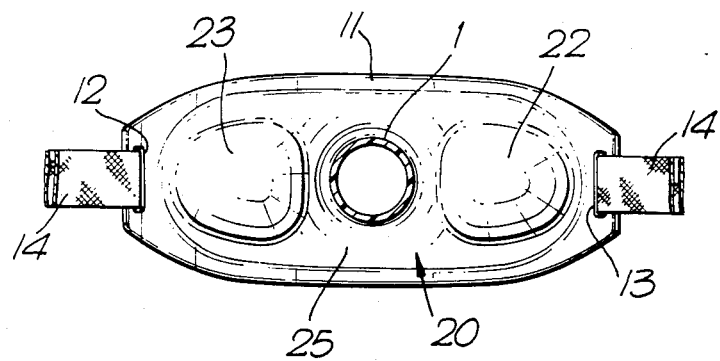
FIG. 2 is a cross-sectional view of the assembly on the line II—II of FIG. 1.

The tracheostomy tube assembly has a plastics tube 1 that is bent at right angles about midway along its length. At its forward, patient end 2 the tube 1 is open and is encompassed by a standard inflatable cuff 3. The cuff 3 can be filled with air via an inflation lumen (not shown), running along the length of the tube within its wall, that communicates with a small bore cuff-inflation line 4 at the rear end 7 of the assembly.

At the rear end 7 of the assembly, the tube 1 opens through a swivel connector 10 which is rotatable about the axis of the tube and which provides a rotatable coupling for tubing (not shown) by which forced ventilation can be effected. Forwardly of the connector 10 and fixed to the tube 1, there is a flange 11 of generally oval shape which extends radially on opposite sides of the tube. The flange 11 is of a soft, semi-flexible material, such as a plastic, and has slots 12 and 13 at opposite ends through which a tape 14 can be threaded to secure the assembly with the patient's neck. Mounted on the forward, patient side of the flange 11 there is an inflatable cuff 20 of PVC which can be inflated by an inflation line 21 that projects from the rear side of the flange. The cuff 20 encircles the tube 1 where it is joined to the flange 11. In its inflated state, the cuff 20 has a rounded raised region, or hill portions 22 and 23 on opposite sides of the tube 1 and a lower, valley portion 24 and 25, intermediate the hill portions, above and below the tube. In its uninflated state, the cuff 20 can lie flat against the flange 11. The cuff is preferably of a soft, floppy material and of a large volume, so that inflation of the cuff can be achieved at low pressure and without elastic deformation of the cuff.

Figure 3:
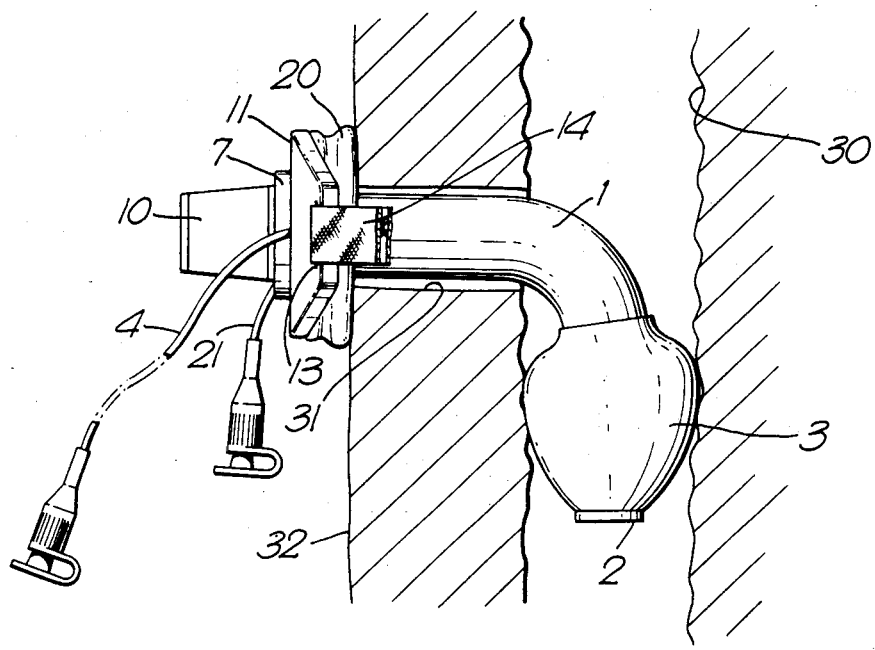
FIG. 3 is a side elevation showing the assembly in use.

In use, the forward, patient end 2 of the assembly is located in the trachea 30 of a patient (as shown in FIG. 3) with the tracheal cuff 3 inflated to seal with the trachea. The rear end 7 of the assembly projects through an opening 31 in the neck 32 of the patient, with the connector 10 and flange 11 spaced from the surface of the neck. A syringe or other similar device (not shown) is connected to the flange cuff inflation line 21 and the flange cuff 20 is inflated until it contacts the surface of the neck. The inflation line 21 is then sealed by a stopper or valve and the flange can be secured by the tape 14 about the neck of the patient.

The location of the flange 11 is selected so that the length of tube 1 forwardly of the flange is sufficient to accommodate the greatest thickness of tissue likely to be experienced between the trachea and neck surface. The cuff 20 is used to bridge the gap between the flange 11 and the neck of those patients with less tissue.

Contact of the cuff 20 with the patient's neck can be sufficiently firm to ensure a stable mounting of the tube, while the cuff 20 provides a comfortable cushion on the patient's neck. A great advantage of the assembly lies in its simplicity of use and in the fact that adjustment of the assembly to patients of different builds can be achieved without discomfort to the patient. Because a syringe or other inflation device is required to inflate the tracheal cuff 3 there is no need to provide additional equipment to inflate the flange cuff 20.

It will be appreciated that the flange cuff may take different shapes and that more than one cuff could be used.

What I claim is:

1. A tracheostomy tube assembly having a tube with a forward end and a rear end, the size and shape of the tube being such that when the forward end is inserted into a patient's trachea through an opening in the patient's neck the rear end projects from the opening, the assembly including a flange by which the tube assembly is secured to the patient's neck, means fixedly securing said flange with said rear end against movement along the tube, the rear end of the assembly including at least one inflatable cuff, and means supporting said cuff at a location externally of the tube and entirely externally of the patient's neck intermediate the flange and the external surface of the patient's neck, said cuff having inlet means whereby fluid can be introduced to the cuff such that any space between the flange and the patient's neck can be accommodated by inflating the cuff.

2. A tracheostomy tube assembly according to claim 1, wherein the said cuff encircles the tube.

3. A tracheostomy tube assembly according to claim 1, wherein the said cuff has a raised portion on opposite sides of the tube.

4. A tracheostomy tube assembly according to claim 1, wherein the volume of the said cuff when inflated is sufficient to accommodate the space between the flange and the neck without elastic deformation of the cuff.

5. A tracheostomy tube assembly according to claim 1, wherein the said cuff is secured to the flange.

6. A tracheostomy tube assembly according to claim 1, wherein the said cuff is of a plastics material.

7. A tracheostomy tube assembly according to claim 1 wherein the said flange is of a soft, semi-flexible material.

8. A tracheostomy tube assembly according to claim 1, wherein the said flange is formed with slots that receive a tape by which the assembly is secured to the patient's neck.

* * * * *